United States Patent [19]

Abecassis et al.

[11] Patent Number: 5,252,708

[45] Date of Patent: Oct. 12, 1993

[54] PREPARATION PROCESS FOR A PROTEIN CONTAINING AT LEAST ONE INTRAMOLECULAR DISULPHIDE BRIDGE BY OXIDATION, AT A PH OF LESS THAN 5.0 OF CORRESPONDING REDUCED RECOMBINANT PROTEIN

[75] Inventors: Pierre Y. Abecassis, Charenton; Jacques Leclaire, Massy; Philippe Riberon, Nogent sur Marne, all of France

[73] Assignee: Roussel Uclaf, Paris, France

[21] Appl. No.: 856,042

[22] PCT Filed: Nov. 23, 1990

[86] PCT No.: PCT/FR90/00843

§ 371 Date: May 6, 1992

§ 102(e) Date: May 6, 1992

[87] PCT Pub. No.: WO92/09623

PCT Pub. Date: Jun. 11, 1992

[51] Int. Cl.$^5$ .............. A61K 45/02; C07K 3/08; C12N 15/26; C12P 21/02
[52] U.S. Cl. ........................ 530/351; 530/410
[58] Field of Search ................. 530/410, 351

[56] References Cited

U.S. PATENT DOCUMENTS

| 4,450,103 | 5/1984 | Konrad et al. | 530/351 |
| 4,530,787 | 7/1985 | Shaked et al. | 530/351 |
| 4,569,790 | 2/1986 | Koths et al. | 530/351 |
| 4,572,798 | 2/1986 | Koths et al. | 530/351 |
| 4,645,830 | 2/1987 | Yasushi et al. | 530/351 |
| 4,752,585 | 6/1988 | Koths et al. | 530/351 |

FOREIGN PATENT DOCUMENTS

| 0185459 | 6/1986 | European Pat. Off. . |
| 0353150 | 1/1990 | European Pat. Off. . |
| 0360937 | 4/1990 | European Pat. Off. . |

OTHER PUBLICATIONS

Creighton, "Methods in Enzymology", Academic Press Inc., (N.Y., U.S.), vol. 107 (1984) p. 314.

Primary Examiner—Michael G. Wityshyn
Assistant Examiner—C. Sayala
Attorney, Agent, or Firm—Bierman and Muserlian

[57] ABSTRACT

Preparation process for a protein comprising at least one intramolecular disulphide bridge, and optionally one or more additional cysteines, comprising the oxidation of the corresponding reduced recombinant protein using an oxidizing agent and characterized in that an aqueous solution of the reduced protein is reacted at a pH of less than 5.0.

11 Claims, 2 Drawing Sheets

PREPARATION PROCESS FOR A PROTEIN CONTAINING AT LEAST ONE INTRAMOLECULAR DISULPHIDE BRIDGE BY OXIDATION, AT A PH OF LESS THAN 5.0 OF CORRESPONDING REDUCED RECOMBINANT PROTEIN

The present invention relates to a preparation process for a protein containing at least one intramolecular disulphide bridge by oxidation, at a pH of less than 5.0, of the corresponding reduced recombinant protein.

Many recombinant proteins for use in therapeutics are expressed in various host systems, amongst which *E. Coli*, yeast and CHO cells represent those most frequently used.

Among these proteins, heterologous proteins expressed but not secreted for example in yeast or in *E. Coli* are generally stored in the form of denatured aggregates in an insoluble granular state. The extraction processes require the latter to be put in solution in a denaturating medium using agents such as urea or guanidine. The correct folding of the molecule, which can then be carried out by various known methods and which is necessary for the protein to exhibit its biological activity, is not always obtained selectively and results in variable yields, often low, according to the recombinant protein concerned due to the associated formation of non-active conformers which must be separated by known purification techniques, for example by chromatography.

In particular when the protein contains at least one intramolecular disulphide bridge, and optionally one or more additional cysteines, the non-secreted recombinant protein is generally produced in a reduced state in the granules. Thus when the restoration of one or more specific disulphide bridges, either necessary for the biological activity of the protein or which contribute to an increase in this activity, is desired, the oxidation process must ensure the correct folding of the protein without formation of the optional undesirable isomers corresponding to the random formation of intramolecular or intermolecular bridges.

One development concerning the regioselective reactions permitting the formation of disulphide bridges from cysteines in peptide chains, obtained by chemical synthesis, describes a multiplicity of methods which highlight the difficulty of optimizing the yields in a general manner and the absence of quantitative results (F, Cavelier et al. Bull. Soc. Chim. Franc. 1989 No. 6 788-798).

Controlled oxidation processes for proteins produced by genetic engineering techniques have been described, notably in the domain of recombinant cytokins containing at least 2 cysteines and produced in *E. Coli*, for example for beta interferon and interleukin 2 (IL2) of which the corresponding natural proteins contain 3 cysteines and a disulphide bridge having a specific position:

the U.S. Pat. No. 4,530,787 describes an oxidation process of completely reduced recombinant proteins illustrated by the application to a reduced mutein of beta interferon which contains 2 cysteines (Example 1), to reduced desAla-IL2 which contains 3 cysteines (Example 3) or to a reduced mutein of desAla-IL2 which contains 2 cysteines (Example 4), using iodosobenzoate at a pH comprised between 5.5 and 9.0, with which, according to the operating conditions, up to 10 to 15% of undesired formed oxidized oligomers are observed.

the U.S. Pat. No. 4,572,798 describe a controlled oxidation using copper chloride at pH 8.0 in the presence of air at 25° C. (Example 2) or at 37° C. (Example 3) of the above mutein of desAla-IL2 whose application to the above reduced desAla-IL2 results in the formation of about 15% of inactive oxidized products having undesired isomer disulphide bridges.

M, P, Weir et al. (Biochem. J 1987 245 85-91) describes an oxidation process of the recombinant IL2 expressed in *E. Coli* in aqueous solution at a concentration of 1 to 2 $\mu$g/ml, in the presence of guanidine, by the action of cupric sulphate at a pH equal to 8.5 which then requires a purification by reversed-phase chromatography in order to obtain the purified IL2. Furthermore the authors indicate that the oxidation becomes "extremely slow" when the pH is lower than 6.

Thus in the absence of a selective quantitative oxidation method for reduced recombinant proteins containing at least 2 cysteines, it is necessary after oxidation at a pH of higher than 5.0 to carry out a purification, generally by chromatography, which eliminates the oxidation products corresponding to the incorrect formation of isomer intramolecular bridges as well as intermolecular bridges.

The obtaining of a homogeneous oxidized recombinant protein therefore poses technical purification problems which result in a lowering of the yield of desired product.

Now it has just been discovered that, in a surprising fashion, the preparation process for a recombinant protein, containing at least one disulphide bridge, does not require a subsequent purification stage to obtain the homogeneous desired oxidized protein and therefore allows the protein to be obtained with an improved Yield if the oxidation is carried out at an acid pH, of less than 5.0.

Therefore the subject of the present invention relates to a preparation process for a protein containing at least one intramolecular disulphide bridge, and optionally one or more additional cysteines, comprising the oxidation of the corresponding reduced recombinant protein using an oxidizing agent and characterized in that an aqueous solution of the reduced protein is reacted at a pH of less than 5.0.

The protein to which the invention relates is a protein chosen from polypeptides having a natural or synthetic amino acid sequence, containing at least one intramolecular disulphide bridge which contributes to the biological activity of the protein and optionally one or more additional free cysteines not engaged in the disulphide bridges, for example calcitonin, insulin, cytokins, cytokin receptors or t-PA which are produced by recombinant DNA technology and isolated in the reduced state, according to known general methods, before the oxidation stage at an acid pH which is the subject of the invention.

By natural protein is meant a protein that can be isolated from natural sources. Indeed it is clear that the process has an entirely general use and can be implemented for the preparation of any protein corresponding to the above criteria.

By reduced state is meant that the cysteines contained by the protein comprise a free sulphhydryl group the determination of which can be made for example by spectrophotometry with dithiodipyridine as thiol reagent.

The oxidizing agent used for the implementation of the invention is chosen from known oxidizing agents which generate an activated oxygen atom, either directly such as an iodosylaryl derivative, for example an iodosobenzoic acid, or indirectly such as iodine in the presence of water or such as a cupric complex, for example the cupric complex formed with o-phenanthroline, or a cupric salt, for example cupric sulphate, in the presence of air, and to the action of which the reduced recombinant protein is subjected, optionally in the presence of air. o.iodosobenzoic acid under an argon atmosphere or cupric sulphate in the presence of air is preferably used as the oxidizing agent.

The concentration of the oxidizing agent varies according to the agent used. For example, when the agent is the direct oxygen donor such as o.iodosobenzoic acid, the concentration is in at least a stoechiometric ratio with the concentration of disulphide bridge to be formed and when the agent directly activates the oxygen, for example the oxygen of the air, such as cupric sulphate, the concentration is lower than or equal to the equivalent concentration of protein to be oxidized.

The temperature of the reaction mixture can be chosen for example between 15° C. and 40° C., preferably at about 37° C.

The duration of the oxidation reaction depends on the above operating conditions. In a general way the reaction is finished in less than 3 hours, preferably about 1 hour.

At the end of the reaction, the desired homogeneous oxidized protein obtained can be directly recovered according to known methods, for example by lyophilization.

The process of the invention relates in particular to a process characterized in that the reduced protein has the amino acid sequence of a natural protein, of alleles or derivatives of the latter.

By alleles or derivatives, there are included sequences modified by substitution or deletion of one or more amino acids other than the cysteines which form the disulphide bridge or bridges naturally containing the desired protein as well as the addition of one or more amino acids, including cysteines which can optionally contribute to the formation of disulphide bridges that do not exist in the natural protein as long as these products preserve the biological activity of the natural protein. The obtaining of such modifications is well known in the recombinant DNA method, for example by the techniques of directed mutagenesis.

The process of the invention relates more particular to a process characterized in that the protein is chosen from cytokins, preferably IL2. The cytokins of the invention can be either cytokins whose natural protein comprises a single disulphide bridge, for example alpha TNF or interleukin 3, or several disulphide bridges, for example alpha interferon, interleukin 6 or GM-CSF, and optionally comprises one or more additional cysteines, for example beta interferon, G-CSF, interleukin 4 or IL2, or the alleles or derivatives of the latter, for example muteins of IL2 as described in the Patent EP 0109748 B or derivatives of IL2 having for example a deletion of one or more amino acids at the N-terminal end as described in the patent application EP 0219839.

The proteins and notably the reduced cytokins necessary for the implementation of the invention are proteins, either directly produced and isolated in the reduced state from the host strain and stabilized in an acid medium for example according to the process described in the patent application EP 0353150, or which are prepared by total reduction of the oxidized protein or a mixture of the oxidized protein and the reduced protein, optionally containing undesired isomer bridges, which can be carried out according to known methods using a reducing agent such as dithiothreitol or mercaptoethanol.

The process of the invention is specially characterized in that the pH is comprised between 0.5 and 5.0, preferably about 3.0. The desired pH of the reaction solution can be obtained using either a mineral acid for example hydrochloric acid or boric acid or an organic acid chosen from monocarboxylic or polycarboxylic acids such as formic, acetic, propionic, trifluoroacetic, oxalic or citric acid, preferably acetic acid.

The process is also characterized in that the protein concentration is comprised between 0.05 mg/ml and 50 mg/ml, preferably between 0.1 and 10 mg/ml.

The process of the invention relates more especially to a process characterized in that the protein is a reduced non-glycosylated recombinant human IL2 having at least 2 cysteines in position 58 and 105.

The above IL2 having at least 2 cysteines in position 58 and 105 can be optionally a recombinant mutein of the natural IL2 in which the cysteine in position 125 has been substituted by another amino acid, for example serine such as IL2-Ser125 that has been described (G. Ju et al, J. Biol. Chem. 262 No. 12 April 25 5723-5731) and whose preparation in reduced form can be obtained for example according to the process described in the Patent Application EP 0353150.

The process of the invention relates quite especially to a process characterized in that the protein is a reduced nonglycosylated recombinant human IL2 having 3 cysteines in position 58, 105 and 125 and which exhibits a biological activity comparable to that of the corresponding oxidized IL2 having a disulphide bridge in position 58-105. Such an IL2 and a preparation example of the latter are described in the patent application EP 0353150.

The preferred conditions of the process of the invention are characterized in that the above reduced IL2 is reacted in solution at about 1 mg/ml, at a pH of about 3.0, at a temperature of about 37° C., in the presence of air with cupric sulphate at a concentration of about 66 $\mu$M. At the end of the reaction, which can be monitored by an analytical method such as the measurement of the consumption of oxygen using a Clark electrode or a reversed-phase high performance liquid chromatography (RP-HPLC) which separates the oxidized form from the reduced starting form, the solution obtained of expected IL2 can then be stored for example at 4° C. or directly lyophilized and optionally be the subject of a pharmaceutical formulation according to known methods.

All the publications that are mentioned are incorporated, by reference, in the text of the present application.

The attached figures illustrate the process described further one:

FIG. 2a represents the solution at t=0 min, FIG. 2b represents the solution at t=15 min, FIG. 2c represents the solution at t=30 min, FIG. 2d represents the solution at t=60 min.

The following example illustrates the invention without however limiting it:

EXAMPLE 1

Oxidation of reduced non-glycosylated recombinant human IL2 (r-hIL2).

1) Experimental Part

The starting reduced r-hIL2 is a "59" fraction prepared according to the process described in Example 1 or 2 of the patent application EP 0353150 in which the citric acid of the linear gradient of isopropanol (20 to 70% over 40 min) is replaced by trifluoracetic acid (TFA) at a concentration of 0.1% and which has been lyophilized immediately at the rate of 1 mg of reduced IL2 per dosage flask.

Figure 1A:
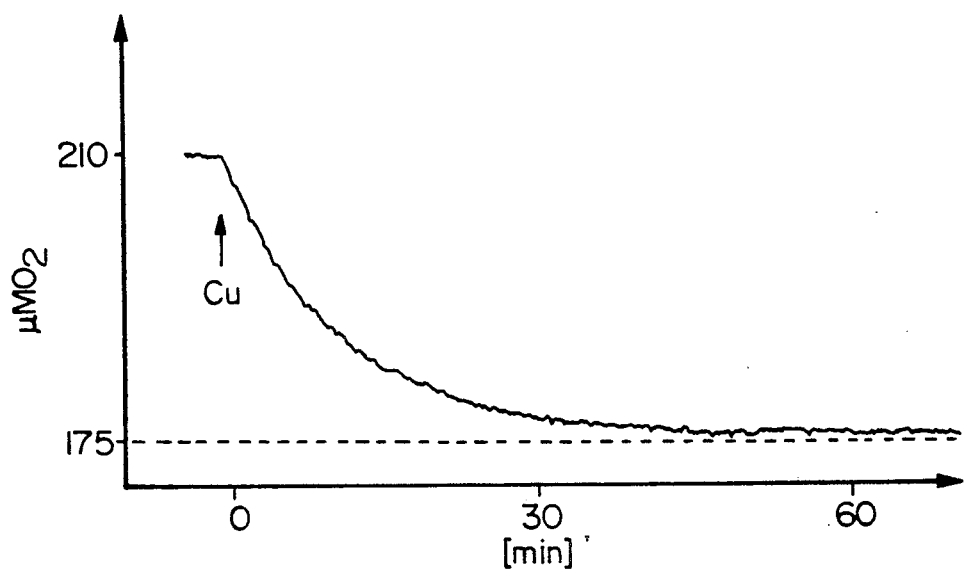
FIG. 1a is the concentration curve in $\mu$Moles of the dissolved oxygen of the reaction solution of Example 1 as a function of time and FIG. 1b is the percentage curve of oxidized IL2 as a function of time, calculated according to the concentration of dissolved oxygen.
Figure 1B:
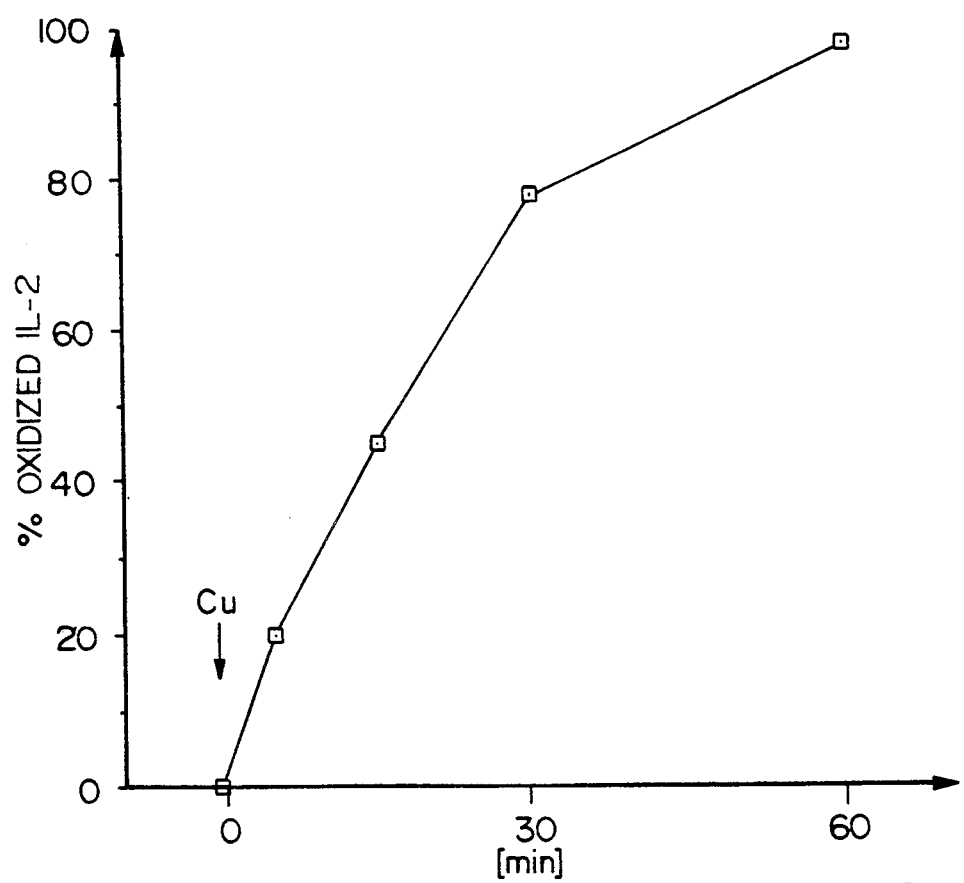
Figure 2A:
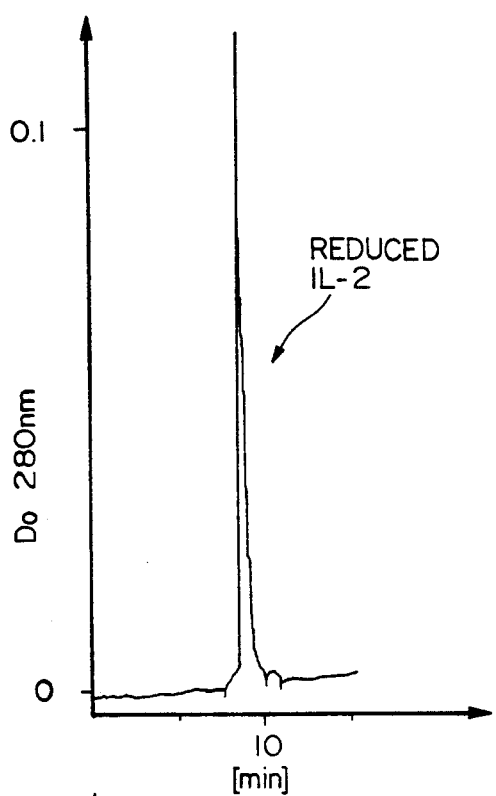
FIGS. 2a to 2d represent 4 chromatograms of analytical RP-HPLC of the reaction solution of Example 1 as a function of time.
Figure 2B:
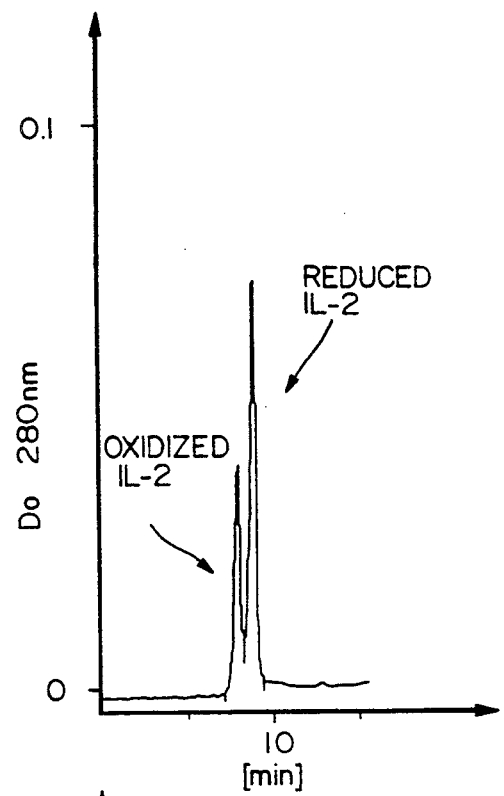
Figure 2C:
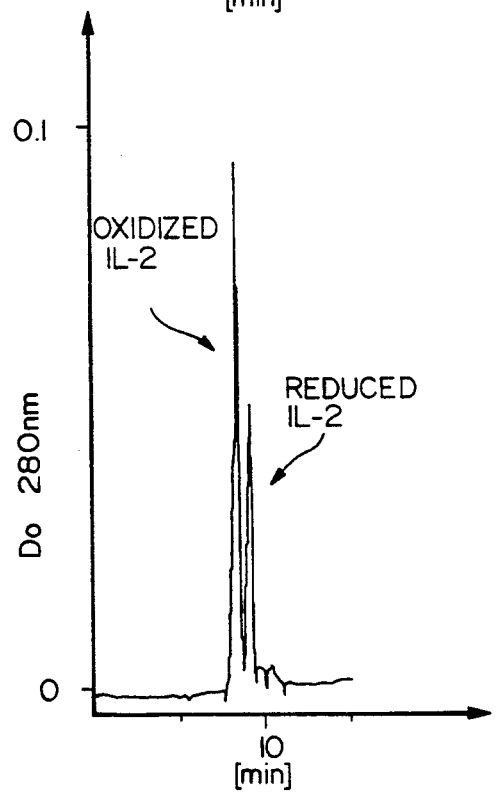

The oxidation of 1 mg of the above reduced IL2 is carried out at 37° C. and at a pH of about 3 by placing in solution in 1 ml of an aqueous solution of acetic acid at a concentration of 0.1% to which 100 μl of a 0.67 mM solution of cupric sulphate is added. The kinetics of the oxidation are monitored on the one hand by continuous measurement of the oxygen consumption using a Clark electrode (FIG. 1a), on the other hand by analytical RP-HPLC on a C4 VYDAC column (0.46×15 cm) 300 A, 5 microns, at a flow-rate of 2 ml/min, with a linear gradient of acetonitrile (30 to 70% over 10 min) containing 0.1% TFA and a spectrophotometric detection at 280 nm of which the surface of the respective peaks of the starting reduced IL2 eluted with about 60% acetonitrile (FIG. 2a) and the oxidized IL2 eluted with about 57% acetonitrile formed during the reaction (FIGS. 2b to 2d) are evaluated.

Figure 2D:
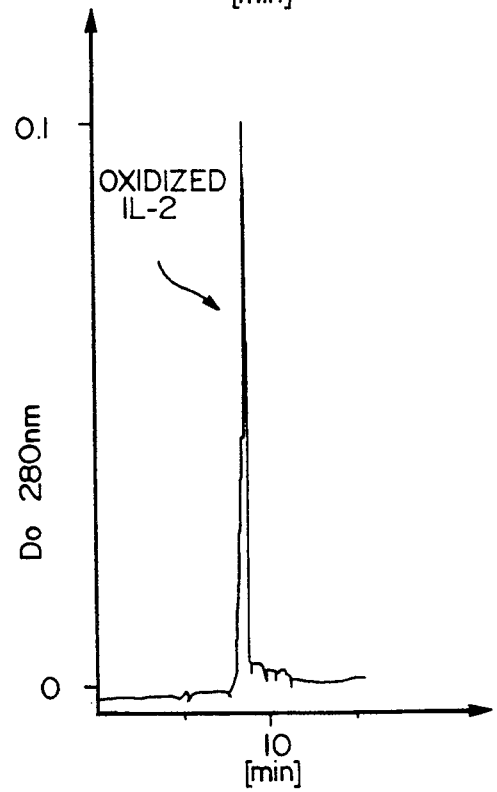

The above figures show that the IL2 is oxidized at about 40% at t=15 min (FIG. 2b), at about 60% at t=30 min (FIG. 2c) and at about 100% at t=60 min (FIG. 2d).

The reaction solution after oxidation at t=60 min is then subjected directly to different analyses.

2) Result of the Analyses the sulphhydryl group content determined by spectrophotometry at 343 nm with dithiodipyridine as thiol reagent is 0.85 SH/mol of obtained oxidized IL2, compared to a content of 2.87 SH/mol of starting reduced IL2.

the location of the disulphide bridge determined according to the method described by Yamada et al. (Arch. Biochem. Biophys. 1987, 257, 194-199) concludes the presence of a disulphide bridge in position 58-105 and a free thiol in position 125.

the biological activity determined by the measurement of the proliferation of leucemic cell lines of IL2 CTLL-2 dependent mice, with a colorimetric test using tetrazolium salt (Mossmann, T J. Immunol. Meth. 1983 65 55-63), is $2.0 \times 10^7$ U BRMP/mg, compared to an activity of $1.5 \times 10^7$ U BRMP/mg for the starting reduced IL2.

We claim:

1. A process for the preparation of a recombinant protein containing at least one intramolecular disulfide bridge and optionally at least one additional cystein comprising oxidizing the corresponding reduced recombinant protein in aqueous solution with an oxidizing agent at a pH of not more than 5.0.

2. The process of claim 1 wherein the reduced protein has the amino acid sequence of a natural protein or alleles thereof.

3. The process of claim 2 wherein the protein is chosen from cytokins.

4. The process of claim 1 wherein the pH is between 0.5 and 5.0.

5. The process of claim 1 wherein the concentration of the protein is between 0.05 mg/ml and 50 mg/ml.

6. Process according to claim 1 wherein the protein is a non-glycosylated reduced recombinant human IL2 having at least 2 cysteines in position 58 and 105.

7. Process according to claim 1 the protein is a non-glycosylated reduced recombinant human IL2 having 3 cysteines in position 58, 105 and 125 and which exhibits a biological activity comparable to that of the corresponding oxidized IL2 having a disulphide bridge in position 58-105.

8. Process according to claim 7, wherein the reduced IL2 is reacted in solution at about 1 mg/ml, at a pH of about 3.0, at a temperature of about 37° C., in the presence of air with cupric sulphate at a concentration of about 66 μM.

9. The process of claim 2 wherein the protein is recombinant IL2.

10. The process of claim 2 wherein the pH is about 3.

11. The process of claim 5 wherein the concentration of the protein is 0.1 to 10 mg/ml.

* * * * *